United States Statutory Invention Registration [19]

Bahl

[11] Reg. Number: H245

[43] Published: Apr. 7, 1987

[54] PLASMID FOR PRODUCING HUMAN INSULIN

[75] Inventor: Chander P. Bahl, El Cerrito, Calif.

[73] Assignee: Cetus Corporation, Emeryville, Calif.

[21] Appl. No.: 625,176

[22] Filed: Jun. 27, 1984

Related U.S. Application Data

[63] Continuation of Ser. No. 278,331, Jun. 29, 1981, abandoned.

[51] Int. Cl.[4] ..... C12P 21/04; C12N 15/00; C12P 21/00; C12N 1/20

[52] U.S. Cl. ..... 435/71; 435/68; 435/172.3; 435/253; 435/317; 435/549; 530/303; 530/808; 935/13; 935/29; 935/47; 935/48; 935/51; 935/56; 935/73

[58] Field of Search ..... 435/253, 68, 70, 172.3, 435/317; 260/112 R, 112 S; 935/13, 29, 47, 48, 51, 56, 73; 530/303, 808

[56] References Cited

FOREIGN PATENT DOCUMENTS

| | | | |
|---|---|---|---|
| 0026598 | 4/1981 | European Pat. Off. | 435/172.3 |
| 0036258 | 9/1981 | European Pat. Off. | 435/172.3 |
| 8000030 | 1/1980 | PCT Int'l Appl. | 435/172.3 |

OTHER PUBLICATIONS

Chan et al., Proc. Natl. Acad. Sci. (US) 78 5401–5405 (1981).

Bell et al., Nature, vol. 282, 525–527 (1979).

Talmadge et al., Proc. Natl. Acad. Sci. (US) 77 3369–3373 (1980).

*Primary Examiner*—John F. Terapane

*Assistant Examiner*—J. E. Thomas

*Attorney, Agent, or Firm*—Albert P. Halluin; Elliott L. Fineman

[57] ABSTRACT

Recombinant plasmids are described that carry the structural gene for human proinsulin in expressible form. The human proinsulin structural gene is fused to a functional transport sequence. Host organisms transformed by the recombinant plasmids express a preproinsulin product that is correctly processed to human proinsulin in vivo, and is transported across the host organism's cell wall. Following its recovery, in vitro methods are used to convert the human proinsulin to human insulin.

10 Claims, 5 Drawing Figures

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

AUTOMATED EDMAN DEGRADATION

PLASMID FOR PRODUCING HUMAN INSULIN

This is a continuation of application Ser. No. 278,331, filed June 29, 1981, abandoned.

This invention relates to molecular biology and more particularly to the so-called art of recombinant DNA. Specifically the invention relates to recombinant plasmids for producing human insulin.

The invention describes novels genetically engineered plasmids that carry a gene coding for human proinsulin. Representative plasmid, pJW2172, illustrates the invention and has been deposited with the American Type Culture Collection, Rockville, Md., 20852; it has been awarded ATCC number 31891. Applicant has directed that the plasmid be freely available to the general public upon the issuance of a U.S. patent.

As is well known, insulin is a peptide hormone that exquisitely regulates a variety of vital metabolic events. In most animals insulin is synthesized as a single large precursor polypeptide, preproinsulin. A transport sequence and an internal peptide sequence are excised from preproinsulin during biosynthesis, yielding a biologically active molecule consisting of two peptide chains linked together by disulfide bonds. Excision of only the transport sequence yields a peptide molecule known as proinsulin. Proinsulins have now been isolated and characterized from a number of animals. See Steiner, D., "Peptide Hormone Precursors" in *Peptide Hormones*, Parsons, J. A., Editor, McMillan Press Limited, London (1976) at pages 49–64.

The beta-cells of the islets of Langerhans produce insulin in vivo. Initially insulin is expressed as a fused polypeptide comprised of the proinsulin sequence plus a pre-sequence known as the transport or signal sequence. This transport sequence facilitates passage of the insulin molecule through the cellular membranes. In the higher eukaryotes, the preproinsulin is synthesized on ribosomes that are associated with the rough endoplasmic reticulum. *See* Permutt, M. and Kipnis, D. M., *Proc. Nat. Acad. Sci.*, USA, 69:506–509 (1972). When it is produced in vivo, the newly translated peptide is first transported intracellularly to the Golgi apparatus where it becomes incorporated within newly forming secretion granules. Exactly how the cell converts proinsulin to insulin is not known, but, conversion is believed to be initiated in either the Golgi apparatus or in the newly formed secretion granules. The secretion granules contain zinc and membrane bound proteases which are believed to participate in the conversion mechanism. The types of proteases can vary from species to species, perhaps to accomodate species specific amino acid substitutions in the insulin peptide. *See* Steiner, supra at 54.

The in vivo production of insulin ultimately results in the secretion of mature insulin molecules from which both the transport sequence and the C chains have been removed. Although it is known that insulin is liberated from the proinsulin in the secretion granules, and that the insulin transport sequence is involved in transport of the peptide across the cell membranes, neither the transport mechanism nor the processing mechanism are well understood.

Because some people fail to produce insulin at all, or fail to produce it in amounts sufficient to meet their own individual needs, it has long been necessary to find supplemental sources of insulin to administer to these people. Most of the supplemental insulin used to treat insulin deficient individuals has come from bovine and porcine pancreata obtained from animals killed at the slaughterhouses. Unfortunately, this animal insulin is immunogenic in some patients. Therefore it would be preferable to have human insulin to administer to those human patients who need it. However, until very recently there was no practical way to obtain enough human insulin to supply the needs of those patients who require it. Although it is possible to chemically synthesize human insulin, on a commercial scale the cost of such production is prohibitive.

Fortunately, recent advances in recombinant DNA technology now make it possible to genetically engineer bacteria so that they can produce eukaryotic proteins such as insulin. For example, Goeddell, D. V., et al., *Proc. Nat. Acad. Sci.*, USA 76:106–110 (1979) chemically synthesized the DNA sequences coding for the human A and B insulin chains. Recombinant techniques were then used to separately ligate each sequence to the 3′ end of an *E. coli* beta-galactosidase gene. As expected, two hybrid proteins were obtained, each consisting of either the human A or B chain fused to the bacterial beta-galactosidase. The A and B chains were released from the fusion peptides by chemical degradation. The chains were purified individually and then recombined to form biologically active insulin. *See* Chance, R. E. et al., *Diabetes Care* 4:147–154 (1981).

Although the Goedell et al technique provides one method of producing human insulin, a more natural approach involves the biosynthesis of proinsulin, which is the immediate precursor of insulin. An advantage of producing insulin from proinsulin is the economy of fermenting and processing only one recombinant organism. The Goeddell et al technique requires the use of two recombinant organisms. Numerous researchers have shown that proinsulin will oxidize spontaneously to form the correct disulfide bonds and can be quantitatively converted to insulin by controlled digestion with trypsin and carboxypeptidase B. *See* Steiner, D. and Clark, J. *Proc. Nat. Acad. Sci.*, USA 60:622–629 (1968); and Kemmler, W. et al. *J. Biol. Chem.*, 246:6786–6791 (1971). Gilbert and his co-workers demonstrated the feasibility of the proinsulin approach when they constructed plasmids in which most of the coding sequences of rat preproinsulin were fused to portions of the prepeptide region of penicillinase. When transformed into *E. coli*, some of these constructs produced fused preproteins that were correctly cleaved to rat proinsulin and segregated into the periplasmic space of the host organism. Analysis of the Gilbert plasmids shows that they contained fusions involving portions of both the penicillinase and the preproinsulin leader sequences. These were usually connected by short interposed sequences derived from the construction process and not related to either presequence. *See* Talmadge, K. et al., *Proc. Nat. Acad. Sci.*, USA 77:3988–3992 (1980).

Although the Gilbert et al experiments demonstrate the feasibility of using the preproinsulin approach to achieve expression of eukaryotic rat insulin, they do not teach how to create a recombinant plasmid carrying the human proinsulin gene in expressible form. Bell, G., et al., *Nature* 282:525–527 (1979) successfully cloned and sequenced the human preproinsulin gene. However, their work does not demonstrate successful expression of the human gene. European Patent Application No. 80300195.4, filed by the Regents of the University of California, incorporates some of the work disclosed in the Bell et al publication, supra. The application itself suggests ways of constructing plasmids carrying the human insulin gene so that the human gene should be expressed. However, the application does not demonstrate actual expression of the human gene and does not indicate how to obtain samples of the plasmid. Furthermore, it does not demonstrate that the human preproinsulin gene product is properly processed by the transformed bacterial host.

Therefore it is an object of the present invention to create a recombinant plasmid carrying the gene for human proinsulin in expressible form.

A further object of the present invention is to create a recombinant plasmid capable of transforming a host organism so that the host will express human proinsulin as a preproinsulin product that will be processed to human proinsulin by the host and then transported across the host's cell membrane.

A further object of the present invention is to demonstrate actual expression of the preproinsulin product by a host organism transformed by a recombinant plasmid carrying the gene for human proinsulin.

Another object of the present invention is to demonstrate that the preproinsulin product expressed by a host organism transformed by a recombinant plasmid carrying the gene for human proinsulin is processed to human proinsulin within the host and then transported across the host's cell membrane.

Other objects of the invention will become apparent to those skilled in the art from the following description, taken in connection with the accompanying drawings wherein.

Figure 1:
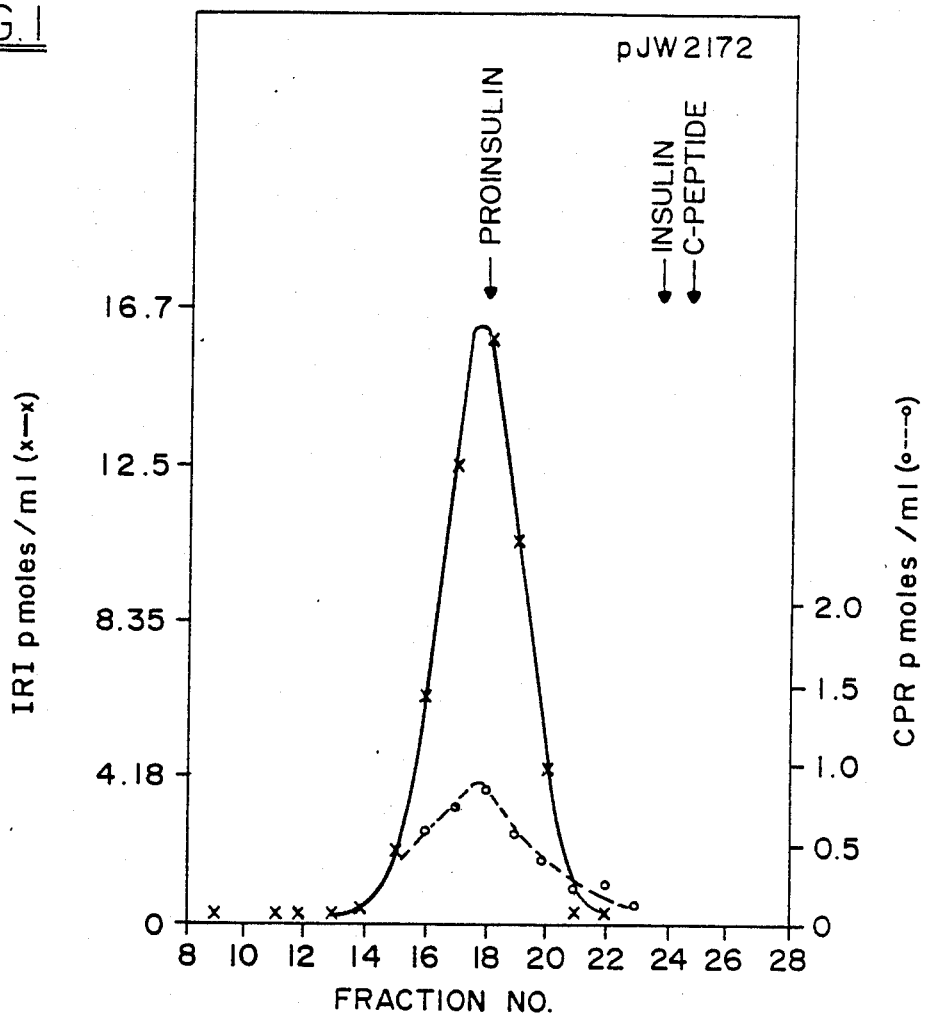
FIG. 1 shows the distribution of immunoreactivity after gel filtration of osmotic shockates from bacterial cultures containing plasmid pJW2172. Elution positions of standard proteins are also indicated.

Very generally, the invention involves construction of novel recombinant plasmids carrying the human proinsulin structural gene in expressible form. Immediately preceeding the eukaryotic proinsulin structural gene on the plasmid is a functional transport presequence. The presequence can be comprised entirely of a prokaryotic bacterial transport presequence, entirely of a eukaryotic transport presequence, or of any functional combination of the two presequence types. The eukaryotic proinsulin structural gene sequence is oriented in the plasmid so that it is in correct translational reading frame with respect to the initiation codon of the functional transport presequence. Such an orientation allows a preproinsulin product to be synthesized by actively metabolizing transformed host organisms. The preproinsulin product is correctly processed to human proinsulin by the transformed host organisms, which then transport the human peptide across the cell membrane. In a transformed *E. coli* host, the human proinsulin accumulates in the bacterial periplasmic space. Following recovery, in vitro methods can be used to convert the human proinsulin to human insulin. *See* Steiner and Clark, supra, and Kemmler et al., supra. Alternatively, the recombinant plasmids could be used to transform host organisms that are not capable of correctly processing preproinsulin to human proinsulin in vivo. In that case the preproinsulin peptide would be recovered by disrupting the transformed hosts' cell walls. The transport sequence portion of the preproinsulin peptide could be removed enzymatically. *See* generally, Zwizinski, C. and Wickner, W., *J. Biol. Chem.* 255:7973–7977 (1980). In vitro methods could then be used to convert human proinsulin to human insulin. *See* Steiner and Clark, supra and Kemmler et al., supra.

More specifically, to illustrate the invention, construction of a representative recombinant plasmid is disclosed. This plasmid, designated as plasmid pJW2172, has been deposited with the American Type Culture Collection, Rockville, Md., 20852, U.S.A. It has been awarded ATCC number 31891. Plasmid pJW2172 was constructed by modifying a parental plasmid, plasmid pHn677, which in turn was derived from the well-characterized plasmid pBR322 (ATCC 37017). Parental plasmid pHn677, which contains human preproinsulin cDNA cloned into the *Pst* I site of the ampicillinase gene of plasmid pBR322, was modified with a restriction endonuclease and a double stranded exonuclease. Large portions of the ampicillinase coding region were excised by these enzymes, resulting in the production of a variety of fused gene segments. Many of these generated proteins were detectable with insulin or C-peptide antisera. One such fused gene segment generating these detectable proteins is carried by plasmid pJW2172. Plasmid pJW2172 contains a perfect fused hybrid gene segment consisting of the amino-terminal coding half of the leader sequence of the prokaryotic ampicillinase (residues −23 to −12) fused to the eukaryotic human preproinsulin prepeptide beginning at residue −13. Expression of the fused segment results in the synthesis of a preproinsulin product, in vivo processing of the preproinsulin product and finally, and secretion of human proinsulin into the periplasmic space of *E. coli* host organisms transformed by plasmid pJW2172. Characterization of the recovered human proinsulin product shows that it contains the A and B chain regions of insulin as well as specific C-peptide immunodeterminants. Tryptic digestion can be used in vitro to convert proinsulin to insulin. *See* Steiner and Clark, supra, and Kemmler et al., supra.

Parental plasmid, pHn677, was obtained originally by cDNA cloning of mRNA isolated from human insulinoma. The cDNA was inserted into the *Pst* I site of pBR322 by means of dC-dG tailing. Plasmid pHn677 contains all of the proinsulin sequence plus the coding sequence for 16 amino acids of the presequence. Although the DNA sequence in the parental plasmid was in the right orientation with respect to the beta-lactamase promoter, it was in the wrong reading frame with respect to the initiation codon of the beta-lactamase gene. As a result there was no expression of the DNA sequence coding for the human proinsulin gene.

Therefore, in order to construct expression plasmids having the cDNA sequence in the correct reading frame, a restriction endonuclease and a double stranded exonuclease had to be used to remove most of the ampicillinase gene upstream from the preproinsulin cDNA sequence. To accomplish this, both parental plasmid pHn677 and progenitor plasmid pBR322 had to be subjected to enzymatic digestion.

Plasmid pHn677 was digested with restriction endonuclease *Pvu* I. The DNA was then treated with double stranded exonuclease Bal 31 to digest approximately 150 nucleotides from each end. This DNA was further treated with restriction endonuclease *Hind* III. After subjecting the resulting DNA to gel electrophoresis on agarose gels, the larger set of DNA fragments was isolated from the gels by electroelution.

In a parallel procedure, *Hinc* II digested plasmid pBR322 DNA was subjected to *Bal* 31 to digest approximately 180 nucleotides from each end of the linearized plasmid. This DNA was then further digested with *Hind* III and *Bam* H1. Finally the fragment containing the beta-lactamase promoter region was isolated from an acrylamide gel. This fragment was ligated to the *Pvu* 1/*Bal* 31/*Hind* III treated large fragment. The ligation mixture was used to transform *E. coli* K12 strain CS412.

Transformants were first screened for tetracycline resistance. Some 350 clones exhibiting such resistance were further examined for insulin expression using the in situ radioimmunoassay procedure described by Broom, S. and Gilbert W., *Proc. Nat. Acad. Sci.*, USA 75:2746–2749 (1978). This procedure showed that 118 of the 350 clones might be expressing insulin. Therefore, these 118 clones were further assayed by means of a radioimmunoassay that utilized both the anti-insulin and the anti-C-peptide antibodies. The radioimmunoassays showed that at least 23 of these clones showed significant, i.e. greater than 1 μunit per ml of insulin activity.

From the total series of plasmids containing a variety of hybrid bacterial-eukaryotic transport sequences attached to the human proinsulin sequence, one plasmid, designated as plasmid pJW2172, was selected for further study. As described in Chan, S. et al *Proc. Nat. Acad. Sci.*, USA 78:5401–5405 (1981), and illustrated here in FIG. 1, gel filtration of a concentrated osmotic shockate i.e., the fluid into which the soluble contents of the cell are released after being subject to osmotic shock, from cultures of transformed bacteria containing plasmid pJW2172gave rise to a single homogeneous peak of C-peptide and insulin immunoreactivity which coeluted at the position of the proinsulin standard. Moreover, the ratio of C-peptide to insulin immunoreactivity of this component, i.e. approximately 1:15, corresponded well to the known cross-reactivity of human proinsulin in the highly specific human C-peptide immunoassay described by Faber, O. K., et al., *Diabetes* 27:170–177 (1978).

These findings are readily explained by DNA sequence analysis of the fused region of plasmid pJW2172. As described more fully in Chan et al., supra, these studies revealed that fusion had occurred between residue −12 of the bacterial ampicillinase leader peptide sequence and residue −13 of the human presequence, thus creating a perfect hybrid leader sequence containing roughly half of each presequence without any substitutions or modifications. This fused leader sequence preserves all of the structural features known to be required for export and cleavage. *See* Faber, et al., supra.

The experiments outlined in the examples that follow demonstrate that plasmid pJW2172 generates a correctly cleaved secreted insulin product.

Example I—Characterization of the Protein Product Secreted by Plasmid pJW2172

As described in Chan et al., supra, the proinsulin material generated by plasmid pJW2172 was characterized in the following manner. A sample of an osmotic shockate, from cultures of bacteria transformed by plasmid pJW2172, containing about 0.05 nM of the peptide was extracted with acid ethanol. The extract was then subjected to gel filtration on a column of Biogel P60 eluted with 2.5 M propionic acid. *See* generally, Steiner, D., et al., in *Cell Biology: A Comprehensive Treatise* 4:175–201 (1980). The tube containing the peak of insulin immunoreactivity, i.e., approximately 0.01 nM, was dried in vacuo and divided into two equal aliquots.

Figure 2:
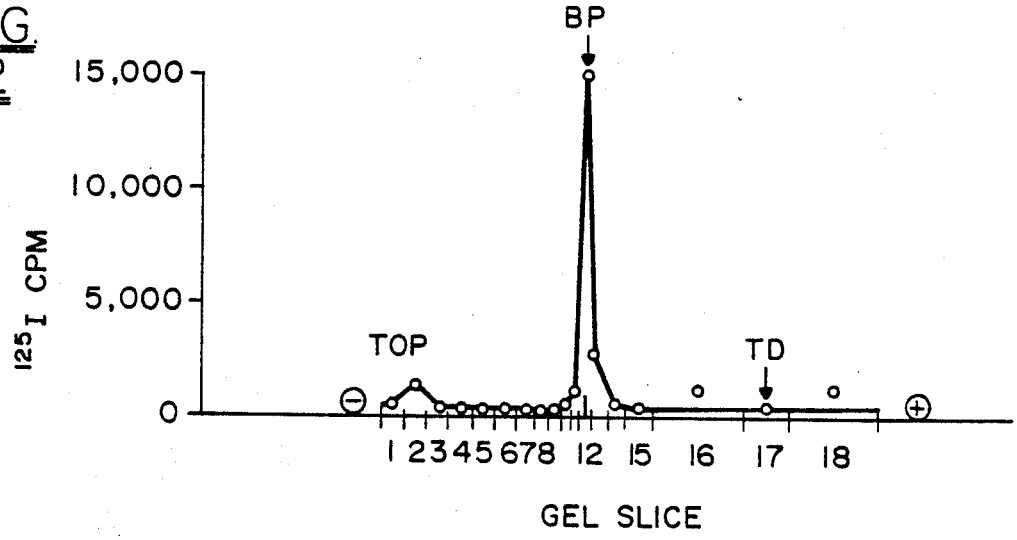
FIG. 2 shows the distribution of radioactivity measured in slices obtained from tube gel SDS electrophoresis of an aliquot of $^{125}$I-labeled immunoprecipitated plasmid pJW2172 product. The vertical bar indicates the position of the stained band of bovine proinsulin.

One aliquot was labeled by iodination and then immunoprecipitated with insulin anti-serum. The resultant immunoprecipitate gave a single peak at the position of proinsulin when examined on a Biogel P30 column eluted with 3 M acetic acid. As shown in FIG. 2, when run on tube gel SDS electrophoresis, the immunoprecipitate migrated as a single component having the same mobility as a bovine proinsulin standard.

Figure 3:
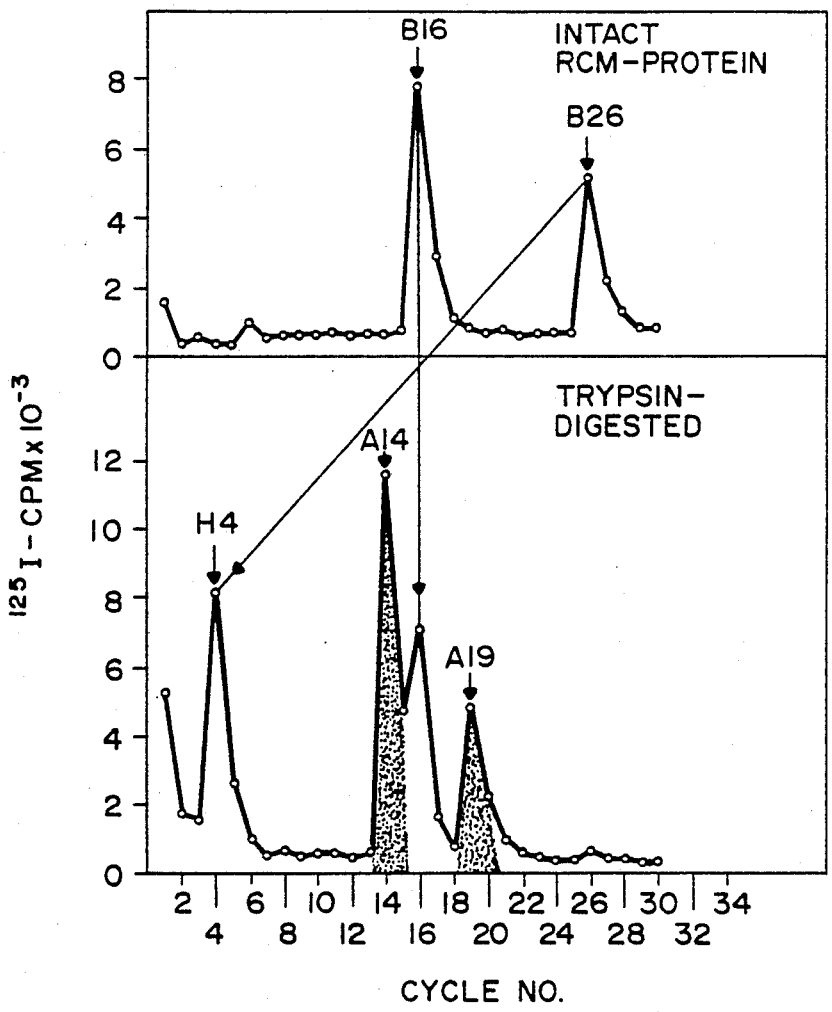
FIG. 3 shows the distribution of radioactivity obtained from automated sequential Edman degradation of $^{125}$I-labeled proinsulin product of plasmid pJW2172.
Figure 4:
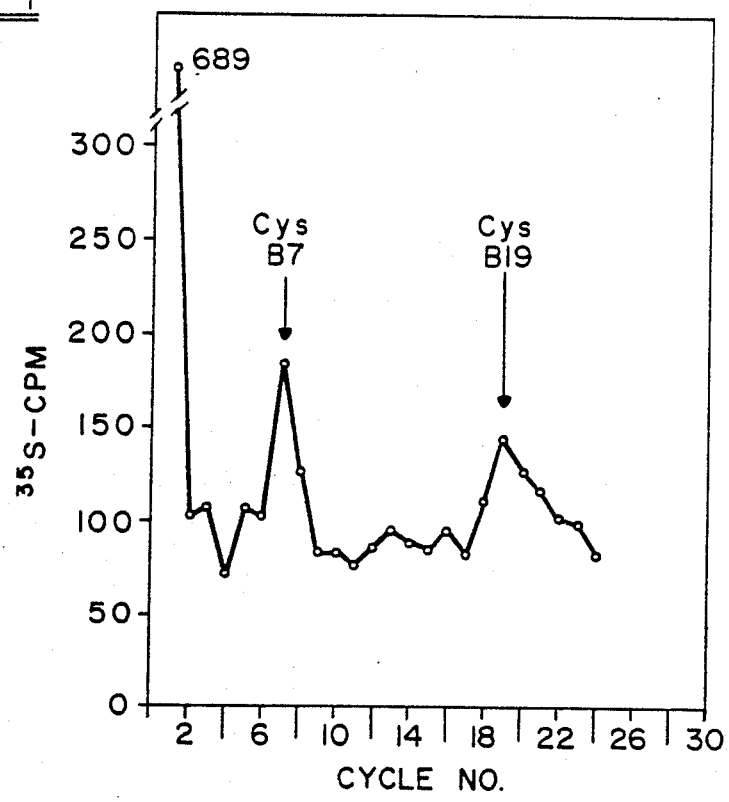
FIG. 4 shows the distribution of radioactivity obtained from automated sequential Edman degradation of $^{35}$S-labeled proinsulin product of plasmid pJW2172.

The second aliquot was used to determine whether cleavage of the presequence had occurred at the first residue of human proinsulin. The 5.0 pM aliquot of the immunoprecipitate was first reduced and carboxymethylated, and then subjected to automated Edman degradation. *See* Chan et al., supra. The results are shown in FIG. 3. They show that significant amounts of radioactively labeled tyrosine were found only at positions 16 and 26, as expected for human proinsulin. There was no indication of heterogeneity at the N-terminus. Further corroboration of this point was obtained when the osmotic shockate from a culture grown in the presence of $^{35}SO_4$ was similarly immunoprecipitated, gel filtered, reduced, carboxymethylated and then sequenced. These results are shown in FIG. 4; they demonstrate the presence of the sulphur labeled B7 and B19 S-carboxymethyl-cysteine residues in correct register.

Example II—Characterization of the Proinsulin Like Peptide

Again, as described more fully in Chan et al., supra, to further characterize the proinsulin like peptide, three additional experiments were performed. In the first, an aliquot of the reduced and carboxymethylated iodinated immunoprecipitate was digested with trypsin and then submitted to automated Edman degradation. These results are shown in FIG. 3. They demonstrate unequivocally that the protein contained the normal human insulin A chain, having tyrosines at position 14 and 19. In addition they show that trypsin had cleaved the B chain region at the arginine located at amino acid position 22, thus generating a heptapeptide that now contained the B26 tyrosine residue at position 4.

Figure 5:
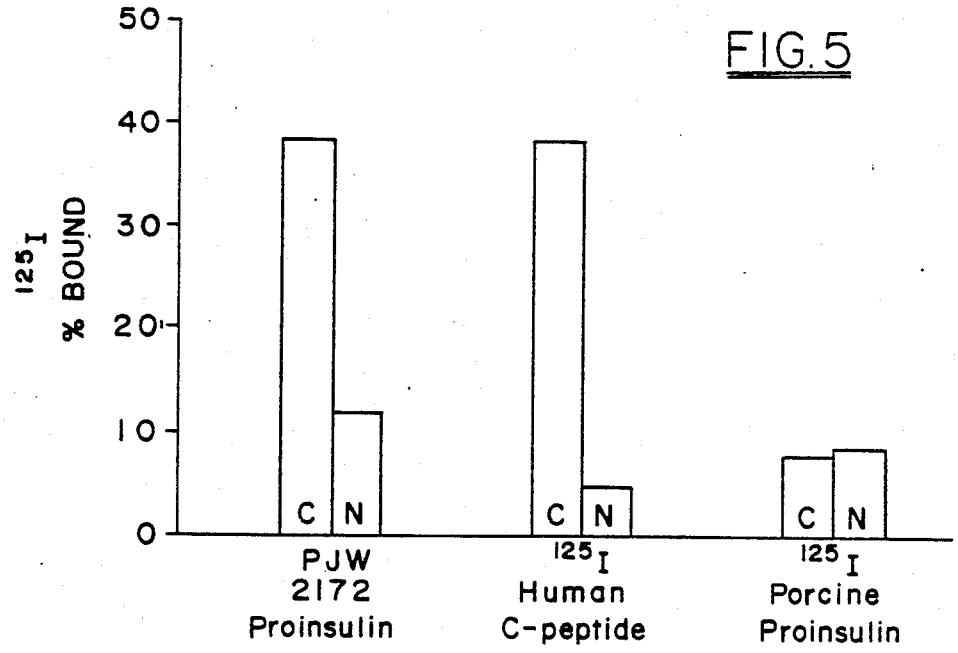
FIG. 5 shows the binding of $^{125}$I-labeled plasmid pJW2172 immunoprecipitated proinsulin to a human C-peptide antiserum. Samples were tested with normal rabbit serum (N) and human C-peptide antiserum (C).

In the second experiment, the presence of C-peptide immunodeterminants in the aliquot material, which had originally been obtained by immunoprecipitation with an insulin antiserum, was assayed by binding to an antiserum against human C-peptide. These results are shown in FIG. 5. They demonstrate that the carboxymethylated protein reacted as well as authentic iodinated human C-peptide. Porcine proinsulin did not bind significantly to this antiserum.

In a third experiment, the plasmid pJW2172 proinsulin product was treated with trypsin and carboxypepsidase B. This treatment converted the product to a component eluting at the position of insulin on gel filtration. There was no indication of the release of free A or B chain material.

On the basis of the evidence discussed in Examples I and II, it is clear that the final protein product generated by host bacteria transformed by plasmid pJW2172 is intact human proinsulin. Using techniques well known to those skilled in the art, it is possible to convert human proinsulin to human insulin in vitro. *See* Steiner and Clark, supra and Kemmler et al., supra.

It may be seen therefore, that the invention involves construction of novel recombinant plasmids carrying the human proinsulin structural gene in expressible form. Immediately preceeding the eukaryotic structural gene on each plasmid is a functional transport presequence. The presequence can be comprised entirely of a prokaryotic bacterial transport presequence, entirely of a eukaryotic transport presequence, or of any functional combination of the two. Representative plasmid pJW2172 carries the human proinsulin structural gene attached to a functional fused hybrid transport presequence. The hybrid transport presequence is comprised of roughly half of the prokaryotic bacterial presequence fused to roughly half of the eukaryotic human presequence. The bacterial presequence codes for the amino-terminal end of the hybrid transport peptide; the human presequence codes for the carboxy-terminal end. *E. coli host becteria transformed by plasmid pJW*2172 express a preproinsulin peptide product that is correctly processed to human proinsulin by the bacteria. This human proinsulin is transported by the bacteria across the cell membrane to the periplasmic space, where it accumulates. Following its recovery, in vitro methods such as tryptic digestion can be used to convert the human proinsulin to human insulin.

Various modifications of the invention in addition to those shown and described herein will become apparent to those skilled in the art from the foregoing description and accompanying drawings. Such modifications are intended to fall within the scope of the appended claims.

REFERENCES

Bell, G. I., Swain, W. F., Pictet, R., Cordell, B., Goodman, H. M., and Rutter, W. J., *Nature* 282:525–527 (1979).

Broom, S. and Gilbert W., *Proc. Nat. Acad. Sci.*, USA 75:2746–2749 (1978).

Chan, S. J., Weiss, J., Konrad, M., White, T., Bahl, C., Yu, S-D., Marks, D., and Steiner, D. F., *Proc. Nat. Acad. Sci.*, USA 78:5401–5405 (1981), Chance, R. E. Kroeff, E. P., Hoffmann, F. A., and Frank, B. H., *Diabetes Care* 4:147–154 (1981).

Faber, O. K., Binder, C., Markussen, J., Heding, L. G., Naithani, V. K., Kuzuya, H., Blix, P., and Rubenstein, A. H., *Diabetes* 27:170–177 (1978).

Goeddell, D. V., Kleid, G. G., Bolivar, F., Heyneker, H. L., Yansura, D. G., Crea, R., Hirose, T., Kraszewski, A., Itakura, K., and Riggs, A. D., *Proc. Nat. Acad. Sci.*, USA 76:106–110 (1979).

Kemmler, W. Peterson, J. D., and Steiner, D. F., *J. Biol. Chem.*, 246:6786–6791 (1971).

Permutt, M. and Kipnis, D. M., *Proc. Nat. Acad. Sci.*, USA 69:506–509 (1972).

Steiner, D. and Clark, J. *Proc. Nat. Acad. Sci.*, USA 60:622–629 (1968).

Steiner, D., Quinn, P. S., Patzelt, C., Chan, S. J., Marsh, J., and Tager, H. S., *Cell Biology: a Comprehensive Treatise* 4:175–201 (1980).

Steiner, D., "Peptide Hormone Precursors" in *Peptide Hormones*, Parsons, J. A., Editor, McMillan Press Limited, London, pp. 49–64 (1976).

Talmadge, K., Kaufman, J., and Gilbert, W., *Proc. Nat. Acad. Sci.*, USA 77:3988–3992 (1980).

Zwizinski, C. and Wickner, W., *J. Biol. Chem.*, 255:7973–7977 (1980).

What is claimed is:

1. A plasmid capable of replication in an *E. coli* host organism, said plasmid comprising a DNA sequence of plasmid pJW2172 encoding the amino acid sequence of the ampicillinase leader peptide-human preproinsulin, said DNA sequence capable of expression in said *E. coli* host transformed with said plasmid to make preproinsulin product comprising a partial ampicillin leader sequence and partial human preproinsulin wherein the partial presequence thereof is perfectly fused to the partial ampicillin leader sequence, wherein said preproinsulin product, when processed in vitro by an *E. coli* host is transported across the host cell membrane to form human proinsulin.

2. A plasmid according to claim 1 which is plasmid pJW2172.

3. An *E. coli* host organism transformed with a plasmid capable of replication in an *E. coli* host organism, said plasmid comprising a DNA sequence of plasmid pJW2172 encoding the amino acid sequence of the ampicillinase leader peptide-human preproinsulin, said DNA sequence capable of expression in said *E. coli* host transformed with said plasmid to make preproinsulin product comprising a partial ampicillin leader sequence and partial human preporinsulin wherein the partial presequence thereof is perfectly fused to the partial ampicillin leader sequence, wherein said preproinsulin product, when processed in vivo by an *E. coli* host is transported across the host cell membrane to form human proinsulin.

4. An *E. coli* host organism according to claim 3 which is capable of correctly processing the preproinsulin product in vivo to human proinsulin and transporting the human proinsulin across the hosts's cell membrane.

5. An *E. coli* host organism according to claim 4 which is *E. coli* strain K–12.

6. An *E. coli* host organism according to claim 5 transformed with plasmid pJW2172.

7. A preproinsulin product coaprising a polypeptide with the amino acid sequence encoded by the sequence of plasmid pJW2172, said polypeptide comprising a partial ampicillinase leader sequence and partial human preproinsulin, said partial presequence thereof perfectly fused to said partial ampicillinase leader sequence, wherein said preproinsulin product, when processed in vivo by an *E. coli* host is transported across the host cell membrane to form human proinsulin.

8. A process for producing human insulin comprising:

(1) providing a plasmid capable of replication in an *E. coli* host organism, said plasmid comprising a DNA sequence of plasmid pJW2172 encoding the amino acid sequence of the ampicillinase leader preproinsulin, said DNA sequence capable of expression in said *E. coli* host transformed with said plasmid to make preproinsulin product comprising a partial ampicillin leader sequence and partial human preproinsulin wherein the partial presequence thereof is perfectly fused to the partial ampicillin leader sequence, wherein said preproinsulin product, when processed in vivo by an *E. coli* host is transported across the host cell membrane to form human proinsulin;

(2) transforming, with the plasmid of step (1), an *E. coli* host organism which is capable of correctly processing the preproinsulin product in vivo to human proinsulin and transporting the human proinsulin across the host's cell membrane;

(3) growing the transformed host organism of step (2) under conditions e for expression of the gene comprising the structural gene which codes for the amino acid sequence encoded by the ampicillinase leader peptide-human preproinsulin-coding DNA sequence of plasmid pJW2172;

(4) allowing the transformed host organism of step (2) to process in vivo the preproinsulin product, expressed from the gene comprising the structural gene which codes for the amino acid sequence encoded by the ampicillinase leader peptide-human preproinsulin-coding DNA sequence of plasmid pJW2172 during the growth of step (3), to human proinsulin and accumulate said human proinsulin outside the host's cell membrane;

(5) recovering the human proinsulin accumulated during the process of step (4);

(6) converting in vitro the human proinsulin recovered in step (5) into human 1nsulin; and (7) purifying the human insulin produced in step (6).

9. A process according to claim 8 wherein the *E. coli* host organism is of *E. coli* strain K-12.

10. A process according to claim 9 wherein the plasmid is pJW2172.

* * * * *